United States Patent
Oh et al.

(10) Patent No.: US 11,003,032 B2
(45) Date of Patent: May 11, 2021

(54) TRANSMITTANCE-VARIABLE DEVICE

(71) Applicant: LG Chem, Ltd., Seoul (KR)

(72) Inventors: Dong Hyun Oh, Daejeon (KR); Eun Jung Lim, Daejeon (KR); Nam Hun Kim, Daejeon (KR)

(73) Assignee: LG Chem, Ltd.

( * ) Notice: Subject to any disclaimer, the term of this patent is extended or adjusted under 35 U.S.C. 154(b) by 0 days.

(21) Appl. No.: 16/607,581

(22) PCT Filed: Apr. 25, 2018

(86) PCT No.: PCT/KR2018/004780
§ 371 (c)(1),
(2) Date: Oct. 23, 2019

(87) PCT Pub. No.: WO2018/199614
PCT Pub. Date: Nov. 1, 2018

(65) Prior Publication Data
US 2020/0050045 A1   Feb. 13, 2020

(30) Foreign Application Priority Data

Apr. 28, 2017 (KR) .......................... 10-2017-0055171

(51) Int. Cl.
*G02F 1/137* (2006.01)
*G02F 1/1347* (2006.01)
(Continued)

(52) U.S. Cl.
CPC ........ *G02F 1/13475* (2013.01); *C09K 19/544* (2013.01); *C09K 19/60* (2013.01);
(Continued)

(58) Field of Classification Search
CPC .................. G02F 1/13475; G02F 1/13725
See application file for complete search history.

(56) References Cited

U.S. PATENT DOCUMENTS

| | | |
|---|---|---|
| 3,900,248 A | 8/1975 | Nagasaki |
| 5,194,973 A | 3/1993 | Isogai et al. |
| | (Continued) | |

FOREIGN PATENT DOCUMENTS

| | | |
|---|---|---|
| EP | 0022311 A1 | 1/1981 |
| JP | S4946954 A | 5/1974 |
| | (Continued) | |

OTHER PUBLICATIONS

Search report from International Application No. PCT/KR2018/004780, dated Jul. 31, 2018.
(Continued)

*Primary Examiner* — James A Dudek
(74) *Attorney, Agent, or Firm* — Lerner, David, Littenberg, Krumholz & Mentlik, LLP

(57) ABSTRACT

A transmittance-variable device is disclosed herein. In some embodiments, the transmittance-variable device includes a first guest host layer, a second guest host layer, and a phase difference element disposed between the first and second guest host layers, wherein each of the first and second guest host layers comprise a liquid crystal host and a dichroic dye guest, and the liquid crystal hosts are capable of being horizontally oriented such that their optical axes are horizontal to each other. The transmittance-variable device can switch between a clear state and a black state, can exhibit high transmittance in the clear state and a high shielding rate in the black state, and can exhibit a high contrast ratio even at the inclination angle. Such a transmittance-variable device can be used in architectural or automotive materials, or eyewear such as goggles for augmented reality experience or sports, sunglasses or helmets.

12 Claims, 3 Drawing Sheets

(51) Int. Cl.
  *C09K 19/54* (2006.01)
  *C09K 19/60* (2006.01)
  *G02B 27/01* (2006.01)
  *G02C 7/10* (2006.01)
  *G02F 1/13363* (2006.01)
  *G02F 1/1337* (2006.01)

(52) U.S. Cl.
  CPC ......... *G02B 27/0172* (2013.01); *G02C 7/101* (2013.01); *G02F 1/1337* (2013.01); *G02F 1/13363* (2013.01); *G02F 1/13725* (2013.01); *G02B 2027/0178* (2013.01); *G02C 2202/16* (2013.01); *G02F 1/133746* (2021.01); *G02F 2201/16* (2013.01); *G02F 2202/043* (2013.01)

(56) References Cited

U.S. PATENT DOCUMENTS

| | | | |
|---|---|---|---|
| 5,625,474 A * | 4/1997 | Aomori | G02F 1/1347 349/139 |
| 5,943,104 A | 8/1999 | Moddel et al. | |
| 2003/0103762 A1 | 6/2003 | Araki et al. | |
| 2010/0092784 A1 | 4/2010 | Kamada et al. | |
| 2011/0205626 A1 | 8/2011 | Saylor et al. | |
| 2013/0094073 A1 | 4/2013 | Ushigome | |
| 2013/0120700 A1 | 5/2013 | Kitson et al. | |
| 2015/0177435 A1 | 6/2015 | Kim et al. | |
| 2015/0269783 A1 | 9/2015 | Yun | |
| 2016/0070132 A1 | 3/2016 | Soto et al. | |
| 2016/0291357 A1 | 10/2016 | Min et al. | |
| 2017/0218686 A1 * | 8/2017 | Galstian | G02F 1/133345 |
| 2017/0276960 A1 | 9/2017 | Osterman et al. | |

FOREIGN PATENT DOCUMENTS

| | | |
|---|---|---|
| JP | S5737329 A | 3/1982 |
| JP | S6325629 A | 2/1988 |
| JP | H04199024 A | 7/1992 |
| JP | H07244293 A | 9/1995 |
| JP | 2003005148 A | 1/2003 |
| JP | 2013101309 A | 5/2013 |
| JP | 2013518301 A | 5/2013 |
| JP | 2019511750 A | 4/2019 |
| KR | 20090098860 A | 9/2009 |
| KR | 20100064437 A | 6/2010 |
| KR | 20150037650 A | 4/2015 |
| KR | 20150105266 A | 9/2015 |
| KR | 20150110285 A | 10/2015 |
| KR | 101612228 B1 | 4/2016 |
| KR | 20170003266 A | 1/2017 |
| KR | 20170037072 A | 4/2017 |
| WO | 99067681 A1 | 12/1999 |
| WO | 2017172277 A1 | 10/2017 |

OTHER PUBLICATIONS

Extended European Search Report including Written Opinion for Application No. EP18791636.6 dated Feb. 13, 2020, 13 pages.

* cited by examiner

[Figure 1]

| 10 |
|---|
| 30 |
| 20 |

[Figure 2]

| 101 |
|---|
| 10 |
| 102 |
| 103 |
| 20 |
| 104 |

[Figure 3]

| 101 |
|---|
| 10 |
| 102 |
| 30 |
| 103 |
| 20 |
| 104 |

[Figure 4]

| 101 |
|---|
| 10 |
| 102 |
| 20 |
| 103 |

[Figure 5]
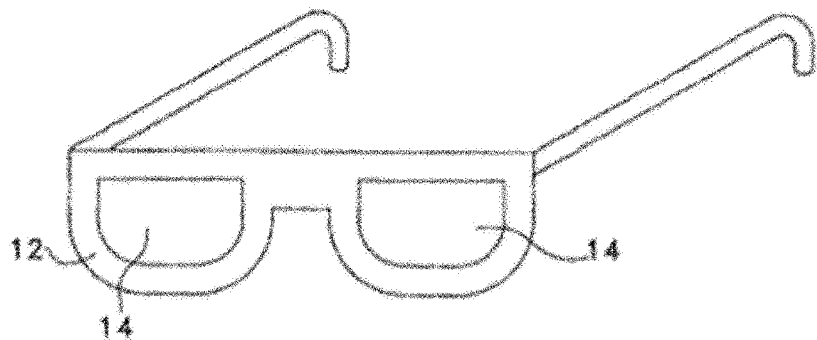
[Figure 6]
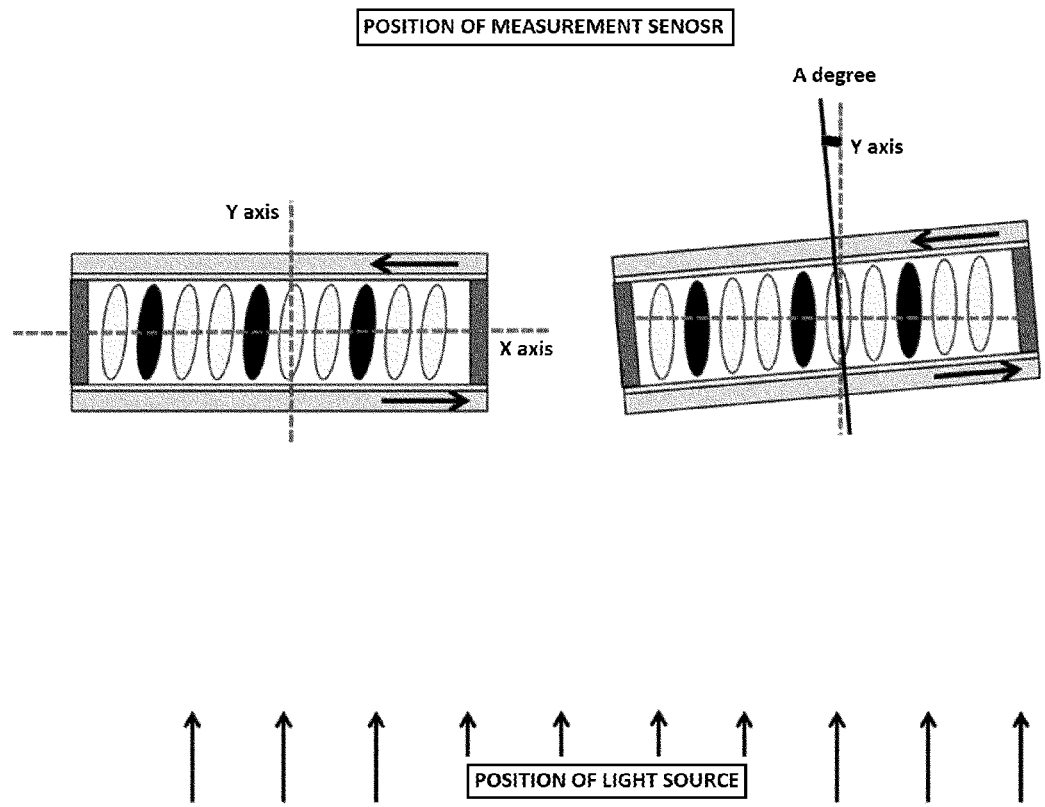

[Figure 7]
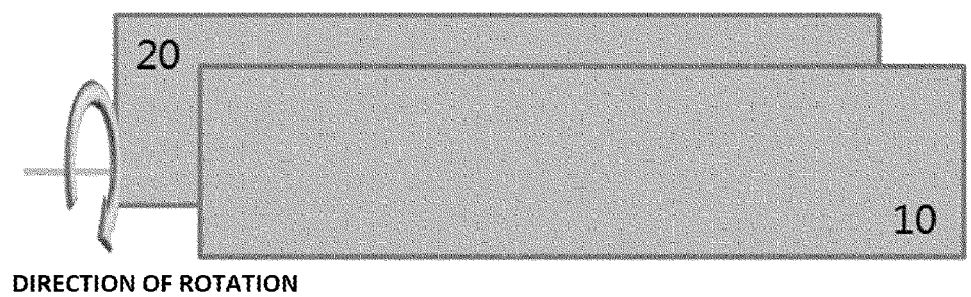
DIRECTION OF ROTATION

TRANSMITTANCE-VARIABLE DEVICE

CROSS-REFERENCE TO RELATED APPLICATION(S)

The present application is a national phase entry under 35 U.S.C. § 371 of International Application No. PCT/KR2018/004780, filed on Apr. 25, 2018, claims priority from Korean Patent Application No. 10-2017-0055171, filed on Apr. 28, 2017, the disclosures of which are incorporated by reference herein.

TECHNICAL FIELD

This application relates to a transmittance-variable device.

BACKGROUND ART

A transmittance-variable device using a so-called GH cell (guest host cell), to which a mixture of a host material, which is mainly a liquid crystal compound, and a dichroic dye guest is applied, is known (for example, Patent Document 1).

Such a transmittance-variable device is applied to various applications including eyewear such as sunglasses, building outer walls, vehicle sunroofs and the like. Recently, application of the transmittance-variable element to eyewear for the so-called augmented reality (AR) experience has been studied as well.

Such a transmittance-variable device adjusts the transmittance by adjusting the orientation of the dichroic dye guest in the GH cell, where there is a case that an observer observes the transmittance-variable device in an oblique direction, depending on the application. The case that an observer observes the transmittance-variable device in an oblique direction is typically a case where the device is mounted on a curved glass or eyewear such as sunglasses or an augmented reality experience device.

However, in the case of the known transmittance-variable devices to date, there is a problem that their contrast ratios (CR) are deteriorated when they are observed in an oblique direction as above.

PRIOR ART DOCUMENTS (Patent Document 1) European Unexamined Patent Publication No. 0022311

BRIEF DESCRIPTION OF DRAWINGS

FIGS. 1 to 4 are schematic diagrams of exemplary transmittance-variable devices of the present application.

FIG. 5 is a schematic diagram of eyewear to which the transmittance-variable device of the present application is applied.

FIGS. 6 and 7 are diagrams for explaining a method of measuring the pretilt angle.

DISCLOSURE

Technical Problem

The present application is directed to a transmittance-variable device, and in one example, it is an object to provide a transmittance-variable device capable of realizing a high contrast ratio even when the transmittance-variable device is observed in an oblique direction, and a use thereof.

Technical Solution

The present application relates to a transmittance-variable device. The term transmittance-variable device may mean a device designed to be capable of switching between a state of high transmittance and a state of low transmittance. As described below, in a structure which comprises at least two guest-host cells (hereinafter, GH cells), the switching between the states can be enabled by adjusting the orientation of the dichroic dye in each GH cell.

In the present application, the state of high transmittance may be referred to as a clear state, and the state of low transmittance may be referred to as a black state. For example, the clear state may mean a state in which the linear light transmittance of the device for vertical light is 40% or more, and the black state may mean a state in which the linear light transmittance of the device for vertical light is 10% or less. Here, in the case where the transmittance-variable device is in the form of a film or a sheet, the vertical light is light incident in a direction parallel to the normal direction of the film or the sheet surface and the linear light transmittance of vertical light is a percentage of the light that is also transmitted in the direction parallel to the normal direction in the vertical light incident on the film or sheet surface.

In another example, the linear light transmittance of the vertical light in the clear state may be about 100% or less, about 95% or less, 90% or less, 85% or less, 80% or less, 75% or less, 70% or less, 65% or less, 60% or less, 55% or less, or 50% or less. In another example, the linear light transmittance of the vertical light in the black state may be about 8% or less, 7% or 6% or less, and also may be 0% or more, 1% or more, 2% or more, 3% or more, or 4% or more.

The transmittance-variable device of the present application can realize high transmittance in a clear state and low transmittance in a black state even when observed in an oblique direction, and accordingly, can realize a high contrast ratio, that is a high ratio (Tc/Tb) of transmittance (Tc) in a clear state to transmittance (Tb) in a black state.

For example, the transmittance-variable device of the present application may have linear light transmittance of oblique light of 40% or more or 45% or more in a clear state. In another example, the linear light transmittance of the oblique light may be about 100% or less, about 95% or less, 90% or less, 85% or less, 80% or less, 75% or less, 70% or less, 65% or less, 60% or less, 55% or less, or 50% or less.

The transmittance-variable device may have linear light transmittance of 10% or less, about 9% or less, about 8% or less, 7% or less, or 6% or less in a black state, and also it may be 0% or more, 1% or more, 2% or more, 3% or more, or 4% or more.

Also, the transmittance-variable device preferably may have a ratio (Tc/Tb) of linear light transmittance (Tc) of oblique light in a clear state to linear light transmittance (Tb) of oblique light in a black state of 7.5 or more, 8 or more, 8.5 or more, 9 or more, 9.5 or more, or 10 or more. In another example, the ratio (Tc/Tb) may be 20 or less, 18 or less, 16 or less, 14 or less, or 12 or less.

Here, in the case where the transmittance-variable device is in the form of a film or a sheet, the oblique light is light incident in a direction forming about 20 degrees to the normal direction of the film or sheet surface, and the linear light transmittance of this oblique light is a percentage of the light transmitted in a direction forming about 20 degrees to the normal direction in the incident light.

The transmittance of the vertical light and the oblique light as mentioned above may be a numerical value for light of any wavelength within a wavelength region of visible light, that is, a wavelength range of 400 to 700 nm, or an average value of numerical values for light of the entire wavelength.

Furthermore, the above-mentioned linear light transmittance in each clear state is the transmittance in a state where the relevant transmittance of the transmittance-variable device is highest, and the linear transmittance in the black state is the transmittance in a state where the transmittance of the transmittance-variable device is lowest.

An exemplary transmittance-variable device can comprise a first GH cell and a second GH cell. In the present application, the term GH cell is a cell comprising a site containing a mixture of a host material and a dichroic dye guest material, which means a cell capable of adjusting the light transmittance by controlling the orientation of the dichroic dye guest in the mixture. Here, as the host material, a liquid crystal compound is generally applied. Hereinafter, in this specification, the host material, which is a liquid crystal compound, may be referred to as a liquid crystal host. Also, the site containing a mixture of a host material and a dichroic dye guest material herein may be referred to as a GH layer. Thus, the first and second GH cells may comprise first and second GH layers, respectively.

In the present application, the first and second GH layers are contained in the device in a state of being superimposed on each other. Accordingly, the light transmitted through the first GH layer can be incident on the second GH layer, and conversely, the light transmitted through the second GH layer can also be incident on the first GH layer.

FIG. 1 is a diagram schematically showing a state where the first GH layer (10) and the second GH layer (20) are superposed on each other as above. Such a structure herein may be referred to as a double cell structure. As shown in FIG. 1, a phase difference element (30) to be described below may exist between the first and second GH layers (10, 20).

In the present application, the first and second GH layers may each comprise at least a liquid crystal compound. The liquid crystal compound may be included as a host material. As the liquid crystal compound, a suitable kind may be selected according to the application without any particular limitation. In one example, a nematic liquid crystal compound can be used as the liquid crystal compound. The liquid crystal compound may be a non-reactive liquid crystal compound. The non-reactive liquid crystal compound may mean a liquid crystal compound having no polymerizable group. Here, the polymerizable group may be exemplified by an acryloyl group, an acryloyloxy group, a methacryloyl group, a methacryloyloxy group, a carboxyl group, a hydroxyl group, a vinyl group or an epoxy group, and the like, but is not limited thereto, and may include known functional groups known as the polymerizable group.

The liquid crystal compound included in the GH layer may have positive dielectric constant anisotropy or negative dielectric anisotropy. In the present application, the term "dielectric constant anisotropy" may mean a difference between an extraordinary dielectric constant ($\varepsilon_e$) and an ordinary dielectric constant ($\varepsilon_o$) of the liquid crystal molecules. The dielectric constant anisotropy of the liquid crystal compound may be, for example, in a range within ±40, within ±30, within ±10, within ±7, within ±5 or within ±3. When the dielectric constant anisotropy of the liquid crystal compound is controlled within the above range, it may be advantageous in terms of driving efficiency of the liquid crystal element.

The refractive index anisotropy of the liquid crystal compound present in the GH layer can be appropriately selected in consideration of the target physical properties, for example, transmission characteristics of the transmittance-variable device, contrast ratios, and the like. The term "refractive index anisotropy" may mean a difference between an extraordinary refractive index and an ordinary refractive index of a liquid crystal compound. The refractive index anisotropy of the liquid crystal compound may be in a range of, for example, 0.1 or more, 0.12 or more or 0.15 or more to 0.23 or less or 0.25 or less or 0.3 or less.

The GH layer may further comprise a dichroic dye. The dye may be included as a guest material. The dichroic dye may serve, for example, to control the transmittance of the device depending on orientation of a host material. In the present application, the term "dye" may mean a material capable of intensively absorbing and/or deforming light in at least a part or all of the ranges within a visible light region, for example, within a wavelength range of 400 nm to 700 nm, and the term "dichroic dye" may mean a material capable of anisotropic absorption of light in at least a part or all of the ranges of the visible light region.

As the dichroic dye, for example, a known dye known to have properties that can be aligned depending on the alignment state of the liquid crystal compound by a so-called host guest effect can be selected and used. An example of such a dichroic dye includes a so-called azo dye, an anthraquinone dye, a methine dye, an azomethine dye, a merocyanine dye, a naphthoquinone dye, a tetrazine dye, a phenylene dye, a quaterrylene dye, a benzothiadiazole dye, a diketopyrrolopyrrole dye, a squaraine dye or a pyromethene dye, and the like, but the dye applicable in the present application is not limited thereto. As the dichroic dye, for example, a black dye can be used. Such a dye is known, for example, as an azo dye or an anthraquinone dye, and the like, but is not limited thereto.

As the dichroic dye, a dye having a dichroic ratio, that is, a value obtained by dividing the absorption of the polarized light parallel to the long axis direction of the dichroic dye by the absorption of the polarized light parallel to the direction perpendicular to the long axis direction, of 5 or more, 6 or more, or 7 or more, can be used. The dye may satisfy the dichroic ratio in at least a part of the wavelengths or any one wavelength within the wavelength range of the visible light region, for example, within the wavelength range of about 380 nm to 700 nm or about 400 nm to 700 nm. The upper limit of the dichroic ratio may be, for example, 20 or less, 18 or less, 16 or less, or 14 or less or so.

The ratio of the dichroic dye in the GH layer can be appropriately selected according to the target physical properties, for example, the transmittance variable characteristics. For example, the dichroic dye may be present in a ratio of 0.01 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, or 1.0 wt % or more in the GH layer. The upper limit of the ratio of the dichroic dye in the GH layer may be, for example, 2 wt % or less, 1.9 wt % or less, 1.8 wt % or less, 1.7 wt % or less, 1.6 wt % or less, 1.5 wt % or less, 1.4 wt % or less, 1.3 wt % or less, 1.2 wt % or less, or 1.1 wt % or less.

The GH layer may further comprise optional addition materials used in the formation of a known GH layer, if necessary, in addition to the components.

The GH layers in the double cells may each have an anisotropy degree (R) of about 0.5 or more at the same time.

The anisotropy degree (R) is measured from absorbance (E(p)) of the light beam polarized parallel to the alignment direction of the liquid crystal host and absorbance (E(s)) of the light beam polarized perpendicularly to the alignment direction of the liquid crystal host according to the following equation.

<Measurement of Anisotropy>

Anisotropy degree $(R)=[E(p)-E(s)]/[E(p)+2*E(s)]$.

The reference used above is another identical device that does not contain a dye in the GH layer.

Specifically, the anisotropy degree (R) may be measured from the value (E(p)) for the absorbance of the GH cell in which the dye molecules are horizontally oriented and the value (E(s)) for the absorbance of the same GH cell in which the dye molecules are vertically oriented. The absorbance is measured in comparison with a GH cell that it does not contain any dye at all but the others have the same configurations. This measurement may be performed using a polarized beam vibrating (E(p)) in a direction parallel to the alignment direction in the case of one vibration plane and vibrating (E(s)) in a direction perpendicular to the alignment direction in the subsequent measurement. The GH cell is not switched or rotated during the measurement, and therefore the measurement of E(p) and E(s) can be performed by rotating the vibration plane of the polarized incident light.

One example of detailed procedures is as described below. The spectra for the measurement of E(p) and E(s) are recorded using a Perkin-Elmer Lambda 1050 UV spectrometer. The spectrometer is equipped with Glan-Thompson polarizers for a wavelength range of 250 nm to 2500 nm in both of the measuring beam and the reference beam. The two polarizers are controlled by a stepping motor and are oriented in the same direction. The change of the polarizer in the polarizer direction, for example, the conversion of 0 degrees to 90 degrees, is always performed synchronously and in the same direction with respect to the measuring beam and the reference beam. The orientation of the individual polarizers may be measured using the method described in T. Karstens' 1973 thesis in University of Wurzburg.

In this method, the polarizer is rotated stepwise by 5 degrees with respect to the oriented dichroic sample, and the absorbance is recorded, preferably, at a fixed wavelength in the maximum absorption region. A new zero line is executed for each polarizer position. For the measurement of two dichroic spectra E(p) and E(s), anti-parallel-rubbed test cells coated with polyimide AL-1054 from JSR are located in both the measuring beam and the reference beam. Two test cells can be selected with the same layer thickness. The test cell containing a pure host (liquid crystal) is placed in the reference beam. The test cell containing a solution of a dye in the liquid crystals is placed in the measuring beam. Two test cells for the measuring beam and the reference beam are installed in a ray path in the same alignment direction. In order to ensure the maximum possible accuracy of the spectrometer, E(p) may be in its maximum absorption wavelength range, for example, a wavelength range of 0.5 to 1.5. This corresponds to transmittance of 30% to 5%. This is set by correspondingly adjusting the layer thickness and/or the dye concentration.

The anisotropy degree (R) can be calculated from the measured values of E(p) and E(s) according to the above equation as shown in a reference [see: "Polarized Light in Optics and Spectroscopy," D. S. Kliger et al., Academic Press, 1990].

In another example, the anisotropy degree (R) may be about 0.55 or more, 0.6 or more, or 0.65 or more. The anisotropy degree (R) may be, for example, about 0.9 or less, about 0.85 or less, about 0.8 or less, about 0.75 or less, or about 0.7 or less.

Such an anisotropy degree (R) can be achieved by controlling the kind of the GH cell, for example, the kind of the liquid crystal compound (host), the kind and the ratio of the anisotropic dye, or the thickness of the GH cell, and the like.

It is possible to provide a film with high contrast ratio by increasing the difference in the transmittance between the transparent state and the black state while using lower energy through the anisotropy degree (R) in the above range.

The first and second GH cells comprising each the GH layer may be superposed on each other to be included in the transmittance-variable device. The liquid crystal host in the GH layer may exist in an oriented state. Depending on the orientation of such a liquid crystal host, the dichroic dye guest may also be oriented. For example, each of the GH cells may have an optical axis. Here, the optical axis means, for example, the average alignment direction of the director of the liquid crystal host material. Here, the alignment direction of the director may mean, in the case of a rod-shaped liquid crystal compound such as a nematic liquid crystal compound, its long axis direction, and may mean, in the case of a disc-shaped compound such as a discotic liquid crystal, the normal direction of the relevant disc plane. The meaning of the optical axis in the GH cell and the manner of determining the relevant optical axis are known, and the known contents as above can be applied in the present application.

For example, the optical axis is usually determined according to the alignment direction of the alignment film, and it can be measured for the GH cell in the following manner. For example, it can be confirmed by disposing a linear polarizer in a state where a GH cell is horizontally oriented on one side of the GH cell and measuring the transmittance while rotating the polarizer 360 degrees. That is, while radiating the light to the GH cell or the linear polarizer side in this state, the direction of the optical axis can be confirmed by measuring the luminance (transmittance) at the other side. For example, when the transmittance is minimized in the process of rotating the polarizer 360 degrees, the angle that is perpendicular or vertical to the absorption axis of the polarizer may be defined as the direction of the optical axis.

In one example, the optical axes of the first and second GH cells in the transmittance-variable device may be vertical or parallel to each GH cell in a state of applying a voltage or a state of applying no voltage. That is, the liquid crystal host of the GH layer in the GH cell may be vertically oriented or horizontally oriented in a state of applying a voltage or no voltage. When the liquid crystal hosts of two GH layers are all horizontally oriented, the optical axes of the liquid crystal hosts of the first and second GH layers can be horizontal to each other. For example, the term vertical, orthogonal, horizontal or parallel in this specification mean substantially vertical, orthogonal, horizontal or parallel, and for example, the meaning of vertical or orthogonal includes the case where there is a deviation within ±10 degrees, within ±9 degrees, within ±8 degrees, within ±7 degrees, within ±6 degrees, within ±5 degrees, within ±4 degrees, within ±3 degrees, within ±2 degrees, within ±1 degree, or within ±0.5 degrees from 90 degrees, and the meaning of horizontal or parallel includes the case where there is a deviation within ±10 degrees, within ±9 degrees, within ±8 degrees, within ±7 degrees, within ±6 degrees, within ±5 degrees, within ±4 degrees, within ±3 degrees, within ±2 degrees, within ±1 degree, or within ±0.5 degrees from 180 degrees. The fact that the optical axis is perpendicular to the GH cell may be the case where the angle formed by the surface of the GH cell and the optical axis is perpendicular or orthogonal and the fact that the optical axis is horizontal to the GH cell may mean that the surface of the GH cell and the optical axis are horizontal or parallel to each other.

For example, when the optical axis of the GH cell is orthogonal to the GH cell in a state of applying no voltage, the optical axis can be oriented parallel to the GH cell by voltage application, and conversely, when the optical axis of the GH cell is parallel to the GH cell in a state of applying no voltage, the optical axis can be oriented so as to be orthogonal to the GH cell by voltage application. In the case where the liquid crystal host is vertically oriented upon applying no voltage as above, an element of a so-called normally transparent mode is realized, and in the case where the liquid crystal host is horizontally oriented upon applying no voltage, an element of a normally black mode is realized. It can be determined depending on the type of the liquid crystal host to be used, the alignment film and/or the position of the electrode layer whether the transmittance-variable device is designed in the normally transparent mode or the normally black mode.

In one example, when the liquid crystal host of the GH layer is vertically oriented, the liquid crystal host may be designed to have a pretilt angle within a predetermined range.

The optical axis of the cell may be designed so as to have a pretilt angle and a pretilt direction within a predetermined range in a state where the optical axis is perpendicular to each GH cell, that is, in a state where the liquid crystal host in the GH cell is vertically oriented.

The pretilt angle of the liquid crystal host may mean the angle formed by the direction of the director of the above-described liquid crystal host with the plane of the GH layer.

The pretilt direction of the first GH cell and the pretilt direction of the second GH cell may be approximately parallel to each other when the liquid crystal hosts of the first and second GH cells all have a pretilt angle of less than 90 degrees.

The pretilt direction may mean the direction in a state where the pretilted liquid crystal host is projected on the GH layer plane.

The method of controlling the pretilt angle and direction of the liquid crystal host in the GH cell as above is not particularly limited, where they can be controlled using, for example, an alignment film.

In one example, the first and second GH cells may further comprise two alignment films disposed on both sides of the first GH layer and the second GH layer, respectively. In one example, the first GH cell may comprise a first vertical alignment film, a first GH layer and a second vertical alignment film sequentially, and the second GH cell may comprise a third vertical alignment film, a second GH layer and a fourth vertical alignment film sequentially.

The pretilt angle and the pretilt direction can be adjusted through control of the alignment direction of the alignment film in the transmittance-variable device of the present application.

The pretilt angle may mean an angle formed by the director of the liquid crystal molecules with respect to a plane horizontal to the surface of the alignment film, the GH layer or the GH cell (hereinafter, the alignment film and the like), or an angle formed with the surface normal direction of the alignment film and the like.

In this specification, the pretilt angle of the alignment film can be used in the same meaning as the pretilt angle of the liquid crystal host, and the pretilt direction of the alignment film can be used in the same meaning as the pretilt direction of the liquid crystal host.

In one example, the first to fourth vertical alignment films may have a pretilt angle in a range of 70 degrees to 90 degrees, or 70 degrees or more but less than 90 degrees. When the pretilt angle is in the above range, it is possible to provide a transmittance-variable device having excellent initial transmittance. In one example, the pretilt angle may be about 71 degrees or more, about 72 degrees or more, about 73 degrees or more, about 74 degrees or more, about 75 degrees or more, about 76 degrees or more, about 77 degrees or more, about 78 degrees or more, about 79 degrees or more, about 80 degrees or more, about 81 degrees or more, about 82 degrees or more, about 83 degrees or more, about 84 degrees or more, about 85 degrees or more, about 86 degrees or more, or about 87 degrees or more, and may be about 88.5 degrees or less, or about 88 degrees or less.

In one example, the pretilt angle of the first vertical alignment film may be an angle measured in a clockwise or counterclockwise direction based on the horizontal plane of the alignment film or the like, and the pretilt angle of the second vertical alignment film may be an angle measured in the reverse direction, that is, the counterclockwise direction when the pretilt angle of the first vertical alignment film is measured in the clockwise direction or the clockwise direction when the pretilt angle of the first vertical alignment film is measured in the counterclockwise direction, or may be an angle measured in the same direction.

Also, the pretilt angle of the third vertical alignment film may be an angle measured in a clockwise or counterclockwise direction based on the horizontal plane of the alignment film or the like, and the pretilt angle of the fourth vertical alignment film may be an angle measured in the reverse direction, that is, the counterclockwise direction when the pretilt angle of the third vertical alignment film is measured in the clockwise direction or the clockwise direction when the pretilt angle of the third vertical alignment film is measured in the counterclockwise direction, or may be an angle measured in the same direction.

The pretilt direction may mean a direction in which the director of the liquid crystal molecules is projected on the horizontal plane of the alignment film.

The pretilt direction of the first and second vertical alignment films and the pretilt direction of the third and fourth vertical alignment films may be horizontal to each other.

In one example, the pretilt angle and direction as mentioned above may be the pretilt angle and direction measured in each GH layer in the case where the GH layer of each GH cell is in a vertical orientation state.

The first to fourth vertical alignment films may be a rubbing alignment film or a photo-alignment film. In the case of the rubbing alignment film, the alignment direction is determined by the rubbing direction, and in the case of the photo-alignment film, it is determined by the polarization direction of the irradiated light. The pretilt angle and the pretilt direction of the vertical alignment film may be realized by adjusting orientation conditions, for example, a rubbing condition or a pressure condition upon rubbing orientation, or optical orientation conditions, for example, a polarizing state of light, an irradiation angle of light, an irradiation intensity of light and the like appropriately.

For example, when the vertical alignment film is a rubbing alignment film, the pretilt angle can be achieved by controlling the rubbing intensity of the rubbing alignment film or the like, and the pretilt direction can be achieved by controlling the rubbing direction of the rubbing alignment film, where this method of achievement is a known method. Furthermore, in the case of the photo-alignment film, they can be achieved by the alignment film material, the direction, state or intensity of the polarized light applied to the orientation.

In the case of using a rubbing alignment film, the rubbing directions of the first and second vertical alignment films may be the same or opposite to each other, and the rubbing directions of the third and fourth vertical alignment films may be the same or opposite to each other.

The rubbing direction can be confirmed through the measurement of the pretilt angle, where since the liquid crystals generally lie along the rubbing direction and generates the pretilt angle, it is possible to measure the rubbing direction by measuring the pretilt angle.

The setting of the pretilt angle and direction as above can be advantageous in realizing higher transmittance in the clear state and lower transmittance in the black state.

When the optical axis orientation of the GH cell as described above and a phase difference element to be described below are combined, it is possible to provide a transmittance-variable device in which the contrast ratio in the oblique direction is greatly improved.

In the transmittance-variable device of the present application, the specific configuration of each GH cell is not particularly limited as long as the GH layer is included in such a configuration.

The transmittance-variable device of the present application comprises at least two GH cells as above, and further comprises a phase difference element disposed between the two GH cells. Accordingly, in the transparent mode, the light may sequentially penetrate the first GH cell, the phase difference element and the second GH cell, or may sequentially penetrate the second GH cell, the phase difference element and the first GH cell.

The specific kind of the phase difference element which can be applied in the present application is not particularly limited. In one example, as the phase difference element, a phase difference element having a λ/2 phase delay characteristic can be used. Here, the phase difference element having a λ/2 phase delay characteristic is an element that if linearly polarized light is incident, the incident light can be converted into linearly polarized light which is approximately orthogonal or orthogonal to the incident light and emitted. The phase difference element may have, for example, a plane phase difference for light with a wavelength of about 550 nm in a range of 200 nm to 350 nm or in a range of 220 nm to 320 nm. Here, the plane phase difference of the phase difference element is a value (d× (nx−ny)) obtained by multiplying the difference (nx−ny) between the refractive index (nx) of the slow axis direction and the refractive index (ny) of the fast axis direction in the phase difference element by the thickness (d).

The phase difference element may be disposed so that when the optical axis of the GH cell is horizontal with respect to the GH cell, the slow axis direction is in a range of about 35 degrees to about 55 degrees, in a range of about 40 degrees to about 50 degrees, or about 45 degrees with the optical axis. It is possible to provide a transmittance-variable device capable of varying the transmittance according to the relationship between the slow axis of the phase difference element and the optical axis of the GH cell as described above, and particularly securing a high contrast ratio even upon observation in the oblique direction.

In the present application, the specific kind of the phase difference element is not particularly limited as long as it has the plane phase difference as above, that is, the λ/2 phase delay characteristic, which may be a single layer or have a laminated structure of two or more layers. For example, the element having the λ/2 phase delay characteristic may also be realized by laminating two sheets of elements having a λ/4 phase delay characteristic. When the phase difference element exhibits the λ/2 phase delay characteristic while having a laminated structure of two or more layers, the slow axis directions of the respective layers in the laminated structure may be parallel or not parallel to each other, but they may be set to directions in which the polarizing direction of the linearly polarized light penetrating the first or second GH layer as a whole can be rotated by 90 degrees and penetrated.

In one example, the phase difference element may be a non-liquid crystal polymer film or a liquid crystal polymer film. Here, the liquid crystal polymer film is a film prepared by orienting and polymerizing a reactive liquid crystal compound known as RM (reactive mesogen) and the non-liquid crystal polymer film is a polymer film having optical anisotropy other than the liquid crystal polymer film, which may mean a polymer film exhibiting optical anisotropy through a process such as uniaxial or biaxial stretching. Such a non-liquid crystal polymer film can be exemplified by a TAC (triacetyl cellulose) film; a COP (cycloolefin copolymer) film such as norbornene derivatives; an acrylic film such as polymethyl methacrylate (PMMA); a polyester film such as a PC (polycarbonate) film or a PET (polyethyleneterephthalate) film; an olefin film such as PE (polyethylene) or PP (polypropylene); a PVA (polyvinyl alcohol) film; a DAC (diacetyl cellulose) film; a Pac (polyacrylate) film; a PES (polyether sulfone) film; a PEEK (polyetheretherketone) film; a PPS (polyphenylsulfone) film, a PEI (polyetherimide) film; a PEN (polyethylenemaphthatate) film; a PI (polyimide) film; a PSF (polysulfone) film; or a PAR (polyarylate), and the like, but is not limited thereto.

The transmittance-variable device of the present application can be realized in various structures as long as it comprises the GH cell including the first and second GH layers and the phase difference element, as described above.

In one example, the transmittance-variable device may comprise first and second substrates disposed to face each other, and third and fourth substrates disposed to face each other. Such a case is shown in FIG. 2. As in FIG. 2, in the transmittance-variable device comprising the first to fourth substrates (101, 102, 103, 104) as above, the first GH layer (10) may be present between the first substrate (101) and the second substrate (102), and the second GH layer (20) may be present between the third substrate (103) and the fourth substrate (104). In the above structure, the second substrate (102) and the third substrate (103) may be arranged to face each other. As shown in FIG. 3, in the structure of FIG. 2, the above-described phase difference element may exist between the second and third substrates (102, 103). In another example, in the structure shown in FIG. 2, the second substrate (102) and the third substrate (103) together may also constitute the phase difference element, without any separate phase difference element. In the structure as in FIG. 3, the second and third substrates (102, 103) may be isotropic substrates. In this case, the second and third substrates (102, 103) are each a substrate exhibiting a λ/4 wavelength phase delay characteristic, where such two substrates may be laminated on each other to form a layer exhibiting the λ/2 phase delay characteristic.

In the structure shown in FIGS. 2 and 3, the sum of the plane phase differences of the second and third substrates (102, 103) existing between the first GH layer (10) and the second GH layer (20) or the sum of the plane phase differences of the second and third substrates (102, 103) and the phase difference element (30) may be in the range capable of exhibiting the above-described λ/2 phase delay characteristic. Here, the sum of the plane phase differences means an optical sum.

In another example, the transmittance-variable device comprises a first substrate (101), a second substrate (102) and a third substrate (103) sequentially arranged as shown in FIG. 4, where the first GH layer (10) may be present between the first and second substrates (101, 102) and the second GH layer (20) may be present between the second and third substrates (102, 103). As shown in FIG. 4, this case is a structure that two GH cells share one substrate (the second substrate (102)). In the case of this structure, the second substrate shared can exhibit the above-described λ/2 phase delay characteristic.

The transmittance-variable device may consist of various structures in addition to the above-exemplified structure as long as the phase difference element as described above can exist between two superimposed GH layers, if possible.

In the above-described structure, a known material can be used as the substrate without any particular limitation. For example, as the substrate, a glass film, a crystalline or amorphous silicon film, an inorganic film such as quartz or ITO (indium tin oxide) film or a plastic film, and the like can be used.

As the plastic substrate, a TAC (triacetyl cellulose) substrate; a COP (cycloolefin copolymer) substrate such as a norbornene derivative substrate; a PMMA (poly(methyl methacrylate)) substrate; a PC (polycarbonate) substrate; a PE (polyethylene) substrate; a PP (polypropylene) substrate; a PVA (polyvinyl alcohol) substrate; a DAC (diacetyl cellulose) substrate; a Pac (polyarylate) substrate; a PES (polyether sulfone) substrate; a PEEK (polyetheretherketone) substrate; a PPS (polyether sulfone), PEI (polyetherimide) substrate; a PEN (polyethylenemaphthatate) substrate; a PET (polyethyleneterephtalate) substrate; a PI (polyimide) substrate; a PSF (polysulfone) substrate; a PAR (polyarylate) substrate or a substrate including an amorphous fluororesin or the like can be used, without being limited thereto. The thickness of such a substrate is not particularly limited, which can be selected within an appropriate range.

An electrode layer may be present on the substrate. For example, the electrode layer may exist on at least one surface of the surfaces facing the GH layer in the surfaces of the substrates included in the transmittance-variable device, for example, at least one surface of the four inner surfaces of the first to fourth substrates in the structure of FIGS. 2 and 3, or any one surface of the inner surfaces of the first and third substrates (101, 103) and both side surfaces of the second substrate (102) in the structure of FIG. 4. In the present application, the term inner surface of the substrate means a surface close to the GH layer among both surfaces of the substrate.

In one example, the electrode layer may exist on at least any one surface of the inner surface of the first substrate (101) and the inner surface of the second substrate (102) and at least any one surface of the inner surface of the third substrate (103) and the inner surface of the fourth substrate (104) in the structure of FIGS. 2 and 3, and if necessary, the electrode layer may exist on all the inner surfaces of the first to fourth substrates so that a vertical electric field can be applied to each GH cell. Also, in the structure of FIG. 4, the electrode layer may exist on at least any one surface of the inner surface of the first substrate (101) and the surface of the second substrate (102) facing the first GH layer (10) and at least any one surface of the inner surface of the third substrate (103) and the surface of the second substrate (102) facing the second GH layer (20), and if necessary, the electrode layer may exist on all the inner surfaces of the first and third substrates and both side surfaces of the second substrate so that a vertical electric field can be applied to each GH cell.

The electrode layer may be formed using a known material, and for example, the electrode layer may comprise a conductive polymer, a conductive metal, a conductive nanowire, or a metal oxide such as ITO (indium tin oxide), and the like. The electrode layer may be formed to have transparency. In this field, various materials and forming methods capable of forming a transparent electrode layer are known, and all of these methods can be applied. If necessary, the electrode layer formed on the surface of the substrate may also be appropriately patterned.

A liquid crystal alignment layer may exist on the substrate. The liquid crystal alignment layer may also be formed on the inner surface of the substrate, that is, the surface facing the GH layer. When the above-mentioned electrode layer is present on the substrate, the liquid crystal alignment layer may also be formed on the surface of the electrode layer or between the electrode layer and the substrate. For example, the liquid crystal alignment layer may exist on at least one surface of the inner surfaces of the substrates included in the transmittance-variable device, for example, at least one surface of the four inner surfaces of the first to fourth substrates in the structure of FIGS. 2 and 3, or any one surface of the inner surfaces of the first and third substrates (101, 103) and both side surfaces of the second substrate (102) in the structure of FIG. 4.

In one example, the liquid crystal alignment layer may exist on at least any one surface of the inner surface of the first substrate (101) and the inner surface of the second substrate (102) and at least any one surface of the inner surface of the third substrate (103) and the inner surface of the fourth substrate (104) in the structure of FIGS. 2 and 3, and if necessary, the liquid crystal alignment layer may exist on all the inner surfaces of the first to fourth substrates. Also, in the structure of FIG. 4, the liquid crystal alignment layer may exist on at least any one surface of the inner surface of the first substrate (101) and the surface of the second substrate (102) facing the first GH layer (10) and at least any one surface of the inner surface of the third substrate (103) and the surface of the second substrate (102) facing the second GH layer (20), and if necessary, the liquid crystal alignment layer may also exist on all the inner surfaces of the first and third substrates and both side surfaces of the second substrate.

As the alignment layer, various horizontal alignment layers or vertical alignment layers known in this field can be applied without particular limitation.

The transmittance-variable device may comprise other necessary elements in addition to the GH cell and the phase difference element as described above. Such elements can be exemplified by antireflection layers or hard coating layers, and the like, but is not limited thereto.

The transmittance-variable device as above can be applied to various applications. The applications to which the transmittance-variable device can be applied can be exemplified by openings in enclosed spaces including buildings, containers or vehicles, and the like, such as windows or sunroofs, or eyewear, and the like. Here, in the range of eyewear, all eyewear formed so that an observer can observe the outside through lenses, such as general glasses, sunglasses, sports goggles or helmets, or instruments for experiencing augmented reality, can be included.

A typical application to which the transmittance-variable device of the present application may be applied is eyewear. Recently, sunglasses, sports goggles, augmented reality experience devices, and the like are commercially available as eyewear in the form in which lenses are mounted so as to be inclined to an observer's frontal line of sight. In the case of the transmittance-variable device of the present application, a high contrast ratio can be ensured even at an inclination angle, as described above, and thus it can be effectively applied to eyewear having the above structure.

When the transmittance-variable device of the present application is applied to eyewear, the structure of the eyewear is not particularly limited. That is, the transmittance-variable device may be mounted and applied in a lens for a left eye and/or a right eye having a known eyewear structure.

For example, the eyewear may comprise a left eye lens and a right eye lens; and a frame for supporting the left eye lens and the right eye lens.

FIG. 5 is an exemplary schematic diagram of the eyewear, which is a schematic diagram of the eyewear comprising the frame (12) and the left and right eye lenses (14), and the eyewear structure to which the transmittance-variable device of the present application can be applied is not limited to FIG. 5.

In the eyewear, the left eye lens and the right eye lens may each comprise the transmittance-variable device. Such a lens may comprise only the transmittance-variable device, or may also comprise other configurations.

The eyewear may have various designs, and for example, the frame may be formed to be inclined so that when an observer wears the eyewear, the angle formed by the observer's front sight line direction and the normal of the surface of the transmittance-variable device is in a range of 15 degrees to 40 degrees. Such eyewear can be exemplified by sports goggles or augmented reality experience devices, and the like.

Advantageous Effects

The transmittance-variable device of the present application can switch between a clear state and a black state, can exhibit high transmittance in the clear state and a high shielding rate in the black state, and can exhibit a high contrast ratio even at the inclination angle. Such a transmittance-variable device of the present application can be applied to various applications including various architectural or automotive materials which need to adjust the transmittance, or eyewear such as goggles for augmented reality experience or sports, sunglasses or helmets.

Mode for Invention

Hereinafter, the transmittance-variable device of the present application will be described in detail by way of examples and comparative examples, but the scope of the present application is not limited by the following transmittance-variable device.

Method for Measuring Pretilt Angle

The pretilt angle of the GH cell can be measured in the following manner. In measuring the pretilt angle of the GH cell, there are a method of measuring it for one GH cell and a method of measuring it in a double cell in which two GH cells are superposed, each of which is described below. Here, the case of the method of measuring it in the double cell is useful for the case where the first to fourth vertical alignment films have all similar pretilt angles. On the other hand, the pretilt direction can be confirmed by disposing an absorptive linear polarizer on one side of the GH cell in a state where each GH cell is horizontally oriented and measuring the transmittance while rotating the polarizer 360 degrees. For example, when the transmittance is minimized in the process of rotating the polarizer 360 degrees, the angle that is perpendicular or vertical to the absorption axis of the polarizer may be defined as the pretilt direction.

1. Measurement of Pretilt Angle of Single GH Cell

First, as shown in FIG. 6, a GH cell is arranged between a light source and a transmittance measurement sensor (for example, LCMS-200). In this state, a direction connecting the measurement sensor and the light source at the shortest distance is defined as a Y-axis, and a direction orthogonal to the Y-axis is defined as an X-axis, as indicated by a dotted line in the drawing. Then, as shown in FIG. 6, the transmittance is evaluated by the measurement sensor while rotating the GH cell and irradiating it with light from the light source. In this process, the orientation state of the GH cell can be maintained in a vertical orientation state. The pretilt angle is measured through the angle formed by the surface normal (indicated by a solid line in the drawing) of the GH cell and the Y-axis at the point where the transmittance becomes maximum when the transmittance is measured through the above process. For example, if the highest transmittance is realized when the Y-axis and the surface normal form A degrees in FIG. 6, the pretilt angle can be defined as a value obtained by subtracting A degrees from 90 degrees. Here, the A degrees is a positive number measured in a clockwise or counterclockwise direction.

2. Measurement of Pretilt Angle of Double Cell

Even in the case of a double cell, the pretilt angle can be measured in the same manner as above. First, as shown in FIG. 7, the double cell is disposed between a light source and a transmittance measurement sensor (for example, LCMS-200). That is, in FIG. 7, the light source is disposed on any one side of the front side (outgoing direction in the drawing) or the rear side (incoming direction in the drawing) of the first GH cell (10), the measurement sensor is disposed on the other side, and the angle (the A degrees) formed by the Y-axis (the axis connecting the light source and the measurement sensor at the shortest distance) and the surface normal of the double cell at the time when the transmittance becomes maximum is measured while rotating the double cell in the rotation direction of the drawing, and then, the value obtained by subtracting the absolute value of the angle from 90 degrees may be defined as a pretilt angle. Even in this case, the orientation of the GH cells (10, 20) can be maintained in the vertical orientation.

Example 1

A first GH cell was produced by forming a GH layer between two COP (cycloolefin polymer) films in which an ITO (indium tin oxide) electrode layer and a vertical alignment film were sequentially formed on the surface. Here, the cell gap of the GH cell was set to about 12 μm. Here, as the vertical alignment film, an alignment film having a pretilt angle of about 89 degrees was used. The alignment film was formed to a thickness of about 200 nm by coating a polyimide-based vertical alignment film on the ITO electrode layer by bar coating, holding the film at 130° C. for about 30 minutes and rubbing the film with a rubbing cloth, and the two COP films were laminated so that the rubbing directions were equal to each other. Also, the GH layer was formed by applying a GH mixture in which nematic liquid crystals having dielectric constant anisotropy of about −4.9 and refractive index anisotropy of about 0.132 as a liquid crystal compound and a black dye having a dichroic ratio of about 6.5 to 8 as a dichroic dye were mixed in a weight ratio of 98.7:1.3 (nematic liquid crystal: dichroic dye). A second GH cell prepared in the same manner as above and the first GH cell were superposed as in FIG. 3, and a COP (cycloolefin polymer) film having a plane phase difference of about 275 nm for a wavelength of 550 nm was placed therebetween to produce a transmittance-variable element. The device is of a type in which the liquid crystal hosts of the first and second GH cells are in a vertical orientation state upon applying no voltage and the liquid crystal hosts are horizontally oriented when a voltage is applied. The lamination of the first and second GH layers was performed such that the optical axes of the liquid crystal hosts in the respective GH layers were horizontal to each other upon the horizontal orientation and the slow axes of the COP films were approximately 45 degrees with the optical axes of the horizontally aligned liquid crystal hosts.

Example 2

The first and second GH cells were prepared in the same manner as in Example 1, except that an isotropic (poly (ethylene terephthalate)) film in which an ITO (indium tin oxide) electrode layer and a vertical alignment film were sequentially formed on the surface and a COP (cycloolefin polymer) film in which an ITO electrode layer and a vertical alignment film were sequentially formed on the surface and the plane phase difference for light having a wavelength of 550 nm was about 137.5 nm, were applied as the substrates upon producing the GH cells, and the cell gap was about 11 µm. Upon producing the GH cell, the slow axis of the COP film was 45 degrees with the optical axis when the liquid crystal host of the GH cell was horizontally oriented. Subsequently, the transmittance-variable device was produced by attaching the COP films of the first and second GH cells such that the slow axes of the respective films were horizontal. The device is of a type in which the liquid crystal hosts of the first and second GH cells are in a vertical orientation state upon applying no voltage and the liquid crystal hosts are horizontally oriented when a voltage is applied. The lamination of the first and second GH layers was performed such that the optical axes of the liquid crystal hosts in the respective GH layers were horizontal to each other upon the horizontal orientation.

Comparative Example 1

A transmittance-variable device was produced in the same manner as in Example 1, except that the COP film as the phase difference element was not applied and the GH cells were laminated such that the optical axes of the respective liquid crystal hosts were perpendicular to each other when both the first and second GH cells were oriented horizontally.

Test Example 1

The transmittance-variable devices produced in Examples and Comparative Examples were irradiated with light of a DC65 light source to evaluate linear light transmittance. When the right horizontal direction was set to 0 degrees and the left horizontal direction was set to 180 degrees, from the center of the transmittance-variable device, the transmittance in the center direction (front), the 0 degree direction, the 90 degree direction, the 180 degree direction and the 270 degree direction was measured to measure the transmittance of all the front and left, right, top and bottom directions. All the devices of Examples and Comparative Examples were in a normally transparent mode exhibiting high transmittance in a state of applying no voltage, the transmittance decreased with applying a voltage, and the minimum transmittance was exhibited upon applying a voltage of about 28V. The transmittance and the contrast ratios of the respective devices according to the applied voltages are summarized in the following table. Table 1 below shows the measurement results for Example 1, and Table 2 shows the measurement results for Example 2. The contrast ratio (CR) is a ratio (Tc/T) of the maximum transmittance (Tc) to the minimum transmittance (T) that is confirmed when the transmittance has been measured while varying the application amount of voltage.

TABLE 1

| Applied Voltage | Front Transmittance | 0 degree Transmittance | 180 degree Transmittance | 90 degree Transmittance | 270 degree Transmittance |
|---|---|---|---|---|---|
| 0 V | 51.4% | 41.8% | 40.6% | 37.5% | 44.8% |
| 2 V | 45.9% | 38.9% | 38.1% | 28.0% | 49.1% |
| 28 V | 2.9% | 4.2% | 3.0% | 2.9% | 3.2% |
| CR | 17.5 | 9.9 | 13.4 | 13 | 15.6 |

TABLE 2

| Applied Voltage | Front Transmittance | 0 degree Transmittance | 180 degree Transmittance | 90 degree Transmittance | 270 degree Transmittance |
|---|---|---|---|---|---|
| 0 V | 54.2% | 44.1% | 44.6% | 41.8% | 47.1% |
| 2 V | 45.0% | 40.2% | 40.5% | 27.5% | 51.6% |
| 28 V | 4.3% | 5.8% | 4.3% | 4.2% | 4.6% |
| CR | 12.7 | 7.6 | 9.4 | 10 | 11.3 |

From the above results, it can be confirmed that the transmittance-variable device of the present application exhibits appropriate transmittance variable characteristics in all the front and the left, right, top and bottom, and the section where the transmittance increases and then decreases is confirmed depending on viewing angles (for example, 270 degrees) while the voltage is applied, whereby it can be applied to various applications.

Test Example 2

The transmittance-variable devices produced in Examples and Comparative Examples were irradiated with light of a DC65 light source to evaluate linear light transmittance. The incident light was irradiated to form an angle of about 20 degrees with the surface normal of the transmittance-variable device. All the devices of Examples and Comparative Examples were in a normally transparent mode exhibiting high transmittance in a state of applying no voltage, the transmittance decreased with applying a voltage, and the minimum transmittance was exhibited upon applying a voltage of about 28V. The transmittance and the contrast ratios of the respective devices according to the applied voltages are summarized in Table 3 below. The contrast ratio is the ratio (Tc/T) of the minimum and maximum transmittance as in Test Example 1.

TABLE 3

|  |  | Example 1 | Comparative Example 1 |
|---|---|---|---|
| Linear light transmittance (%) | 0 V | 45.9 | 46.3 |
|  | 11 V | 6.9 | 7.9 |
|  | 15 V | 6.1 | 7.2 |
|  | 20 V | 5.7 | 6.7 |
| Contrast ratio | 11 V | 6.7 | 5.9 |
|  | 15 V | 7.5 | 6.5 |
|  | 20 V | 8.1 | 6.9 |

From the results shown in Table 3, it can be confirmed that the transmittance-variable device according to the present application can realize high transmittance in the clear state and low transmittance in the black state even for the oblique light.

EXPLANATION OF REFERENCE NUMERALS

10: first GH layer
20: second GH layer
30: phase difference element
101, 102, 103, 104: substrate
14: left eye or right eye lens
12: frame

The invention claimed is:

1. A transmittance-variable device, comprising:
a first substrate;
a first guest host layer;
a second substrate constituting a phase difference element;
a second guest host layer; and
a third substrate;
wherein the first substrate, the first guest host layer, the second substrate, the second guest host layer, and the third substrate are sequentially disposed,
wherein each of the first and second guest host layers comprise a liquid crystal host and a dichroic dye guest, and the liquid crystal hosts of the first and second guest host layers are capable of being horizontally oriented such that their optical axes are parallel to each other,
wherein the second substrate has a plane phase difference for light having a wavelength of 550 nm in a range of 200 nm to 350 nm, and
wherein the phase difference element has a $\lambda/2$ phase delay characteristic.

2. The transmittance-variable device according to claim 1, wherein the device is capable of switching between a clear state and a black state depending on application of a voltage.

3. The transmittance-variable device according to claim 2, wherein a ratio (Tc/Tb) of transmittance (Tc) of incident light through the device in the clear state and transmittance (Tb) of the incident light through the device in the black state is 7.5 or more, wherein the incident light forming an angle of 20 degrees with the normal of the surface of the guest host layer.

4. The transmittance-variable device according to claim 1, wherein the liquid crystal host comprises a nematic liquid crystal compound.

5. The transmittance-variable device according to claim 1, wherein the dichroic dye is an azo dye, an anthraquinone dye, a methine dye, an azomethine dye, a merocyanine dye, a naphthoquinone dye, a tetrazine dye, a phenylene dye, a quaterrylene dye, a benzothiadiazole dye, a diketopyrrolopyrrole dye, a squaraine dye or a pyromethene dye.

6. The transmittance-variable device according to claim 1, wherein when the liquid crystal hosts in the first and second guest host layers are horizontally oriented when no voltage is applied, the liquid crystal hosts are converted to a vertical orientation state when a voltage is applied, and
wherein when the liquid crystal hosts are horizontally oriented when a voltage is applied, the liquid crystal hosts are converted to a vertical orientation state when no voltage is applied.

7. The transmittance-variable device according to claim 6, wherein the liquid crystal hosts in the vertical orientation state have a pretilt angle in a range of 70 degrees or more and less than 90 degrees.

8. The transmittance-variable device according to claim 7, wherein a pretilt direction of the first guest host layer and a pretilt direction of the second guest host layer are parallel to each other.

9. The transmittance-variable device according to claim 1, wherein an angle formed by a slow axis of the phase difference element and an optical axis of the liquid crystal hosts in the first and second guest host layers upon horizontal orientation is in a range of 35 degrees to 55 degrees.

10. The transmittance-variable device according to claim 1, wherein the phase difference element is a non-liquid crystal polymer film or a liquid crystal polymer film.

11. Eyewear, comprising:
a left eye lens and a right eye lens; and
a frame for supporting the left eye lens and the right eye lens,
wherein the left eye lens and the right eye lens each comprise the transmittance-variable device of claim 1, and
wherein an angle formed by a front sight line direction of an observer at the time of wearing and the normal of the surface of the transmittance-variable device is in a range of 15 degrees to 40 degrees.

12. The eyewear according to claim 11, wherein the eyewear is an augmented reality experience device.

* * * * *